(12) United States Patent
Nishina

(10) Patent No.: US 7,661,325 B2
(45) Date of Patent: Feb. 16, 2010

(54) TEST PIECE MAGAZINE, MAGAZINE HOLDER, AND TEST PIECE ATTACHMENT APPARATUS

(75) Inventor: Rintaro Nishina, Yamagata (JP)

(73) Assignee: Sousei Electronics Corporation (JP)

( * ) Notice: Subject to any disclaimer, the term of this patent is extended or adjusted under 35 U.S.C. 154(b) by 0 days.

(21) Appl. No.: 11/955,702

(22) Filed: Dec. 13, 2007

(65) Prior Publication Data

US 2009/0151448 A1 Jun. 18, 2009

(51) Int. Cl.
*G01N 1/00* (2006.01)
(52) U.S. Cl. ........................................ 73/863
(58) Field of Classification Search ........................ None
See application file for complete search history.

(56) References Cited

U.S. PATENT DOCUMENTS

| | | | |
|---|---|---|---|
| 5,632,410 A | | 5/1997 | Moulton et al. |
| 5,975,349 A | * | 11/1999 | Menes ................ 221/232 |
| 6,135,314 A | * | 10/2000 | Menes ................ 221/232 |
| 2003/0002387 A1 | * | 1/2003 | Bottwein et al. ............ 366/273 |
| 2004/0007585 A1 | | 1/2004 | Griffith et al. |
| 2005/0281706 A1 | * | 12/2005 | Funke et al. ............ 422/63 |

FOREIGN PATENT DOCUMENTS

| | | |
|---|---|---|
| JP | 60-79265 A | 5/1985 |
| JP | 62-30962 A | 2/1987 |
| JP | 63-250564 A | 10/1988 |
| JP | 8-285858 A | 11/1996 |
| JP | 2003-344424 A | 12/2003 |
| JP | 3684458 | 6/2005 |
| JP | 3738357 | 11/2005 |

OTHER PUBLICATIONS

Notice of Grounds for Rejection for Japanese Patent Application No. 2006-157603 mailed Apr. 28, 2009 with English translation.

* cited by examiner

*Primary Examiner*—Robert R Raevis
(74) *Attorney, Agent, or Firm*—Cantor Colburn LLP

(57) ABSTRACT

A test piece attachment apparatus includes a test piece magazine having an inner space storing a plurality of specimen component test pieces aligned in a predetermined direction and a feed outlet via which the specimen component test pieces can be successively extruded, a magazine holder exchangeably holding the test piece magazine, a torsion spring generating a bias force to press the specimen component test pieces aligned in the test piece magazine toward the feed outlet, and a cylindrical casing. The cylindrical casing includes a recessed groove that allows the magazine holder to move in its axial direction and an extrusion projection disposed at a position where the extrusion projection can push one specimen component test piece positioned at the feed outlet and can extrude the specimen component test piece out of the test piece magazine in accordance with a movement of the magazine holder.

6 Claims, 10 Drawing Sheets

TEST PIECE MAGAZINE, MAGAZINE HOLDER, AND TEST PIECE ATTACHMENT APPARATUS

BACKGROUND OF THE INVENTION

1. Field of the Invention

The present invention relates to a test piece magazine, a magazine holder, and a test piece attachment apparatus. Particularly, the present invention relates to a test piece magazine that stores a plurality of specimen component test pieces, a magazine holder that exchangeably holds a test piece magazine, and a test piece attachment apparatus operable to send and attach a specimen component test piece to a portable specimen analyzer that has a distal end portion configured into a test piece holding portion capable of holding a specimen component test piece.

2. Description of the Related Art

Coloring agent test pieces are conventionally used to simply analyze various components contained in human and/or animal body fluids (blood, sweat, urine, etc), or components contained in a variety of water sources (drinking water, contaminated water, etc). Litmus paper, as a representative coloring agent test piece, may have a sticklike (paper board) base and a test patch attached to one end of the base. When a user pours a liquid-state specimen on the test patch, a reagent contained in the test patch changes color. Thus, a user can analyze a component contained in the specimen based on the color change.

For example, as a method for checking a blood sugar value using a non-invasive blood vessel, a urine component test piece can be used to measure a urine sugar value. The urine component test piece also has a sticklike (paper board) base with a test patch attached on one end thereof. When the test patch is exposed to urine, a reagent in the test patch changes color according to the sugar (glucose) content in the urine. In general, a relationship between the tone of coloring and a urine sugar value can be defined using a standard color tone table which determines a color tone mark, such as −, ±, (+), +, ++, +++, according to the tone of coloring. For example, if the color tone mark is ±, the urine sugar value is at a level of 50 mg/deciliter. As described above, the urine component test piece is suitable for simple measurement of a urine sugar value and enables a user to check their own blood sugar value.

However, the reaction of a specimen component test piece (i.e., a coloring agent test piece) is a chemical reaction which is significantly effected by elapsed time and color tone conditions of a specimen (urine, drainage, etc). Hence, as discussed in Japanese Patent No. 3,738,357, the applicant of this invention has proposed a portable specimen analyzer including a specimen gathering bath, a specimen detector, a timer that measures elapsed time in the specimen detection, and a sensing portion that detects a change of color.

Furthermore, if an optical sensor is used to detect a reaction of a specimen component test piece, external light may have an adverse effect on the measurement results. Hence, as discussed in Japanese Patent No. 3,684,458, the applicant of this invention has proposed a coloring agent test piece possessing light-shielding properties, according to which at least one surface of a sticklike base is a black surface and a test patch is attached on this base.

According to the above-described portable specimen analyzer discussed in Japanese Patent No. 3,738,357, the specimen gathering bath enables a specimen component test piece to reliably absorb a liquid-state specimen and the timer can perform a time management of a coloring reaction. Thus, the analysis can obtain a reproducible result. Furthermore, the sensing portion can objectively determine a specimen component without relying on a user's individual judgment. Moreover, the coloring agent test piece discussed in Japanese Patent No. 3,684,458, i.e., a specimen characteristic test piece, can suppress or eliminate adverse effects of external light.

In view of usability, the portable specimen analyzer discussed in Japanese Patent No. 3,738,357 can be further improved to enable a user to easily attach a specimen characteristic test piece to the analyzer. Furthermore, in view of performance, it is preferable that a specimen component test piece having light-shielding properties (i.e., the test piece discussed in Japanese Patent No. 3,684,458) can be easily attached.

SUMMARY OF THE INVENTION

The present invention is directed to a test piece attachment apparatus that simplifies attachment of a specimen component test piece to a portable specimen analyzer. Furthermore, the present invention is directed to a test piece magazine that can store a plurality of specimen component test pieces. Moreover, the present invention is directed to a magazine holder that holds a test piece magazine in an exchangeable manner.

A test piece magazine according to the present invention is capable of storing a plurality of specimen component test pieces aligned in a predetermined direction under an external bias force and extruding a specimen component test piece via a feed outlet under an external extrusion force. The test piece magazine includes a boxlike casing having an inner space storing a plurality of specimen component test pieces aligned in a thickness direction; an aperture formed in at least a rear side surface portion of the boxlike casing to which a rear side surface of a biasing plate faces, and supplying a bias force to the biasing plate; a test piece outlet formed at an upper surface portion of the boxlike casing via which a foremost specimen component test piece can be extruded in an up-and-down direction; and a slit provided in a front side surface portion of the boxlike casing to which the specimen component test pieces are pressed and extending in an up-and-down direction with a uniform width for supplying an extrusion force to extrude the specimen component test piece upward. At a lower surface portion of the boxlike casing, the slit has an extrusion length as an aperture length in the thickness direction of the specimen component test piece. The extrusion length is equivalent to the sum of the thicknesses of the front side surface portion of the boxlike casing and the specimen component test piece. On the upper surface portion of the boxlike casing, the slit is connected to the test piece outlet and has a length corresponding to the extrusion length as an aperture length in the thickness direction of the specimen component test piece. The external extrusion force can be applied to the specimen component test piece using an extrusion surface defined by the extrusion length and the slit width.

It is preferable that, in the test piece magazine according to the present invention, the length of the inner space of the boxlike casing in an alignment direction of the specimen component test pieces is equivalent to the sum of the thickness of the biasing plate and a maximum length of aligned specimen component test pieces storable in the boxlike casing.

It is preferable that, in the test piece magazine according to the present invention, the biasing plate is disposed in the inner space of the boxlike casing, with one side face of the biasing plate contacting a rearmost specimen component test piece and the other side surface of the biasing plate receiving the bias force applied to the specimen component test pieces in the alignment direction.

It is preferable that, in the test piece magazine according to the present invention, the biasing plate has an outer shape and dimensions similar to those of the specimen component test piece, such that the biasing plate can be extruded via the feed outlet when the external extrusion force is applied to the biasing plate.

It is preferable that, in the test piece magazine according to the present invention, a marking is provided on a rearmost specimen component test piece which is finally extruded to enable a user to discriminate the rearmost specimen component test piece from other specimen component test pieces when the boxlike casing stores the plurality of specimen component test pieces aligned in the thickness direction.

A magazine holder according to the present invention may be configured to exchangeably hold a test piece magazine that can store a plurality of specimen component test pieces aligned in a predetermined direction under an external bias force. The magazine holder includes a framed casing that guides and supports side surfaces of the test piece magazine and has a storage space for exchangeably storing the test piece magazine; an urging member that presses the specimen component test pieces stored in the test piece magazine in a predetermined direction; and an installation portion provided on the framed casing for mounting the urging member.

It is preferable that, in the magazine holder according to the present invention, the installation portion is provided on a bottom surface portion of the framed casing, and the urging member is a torsion spring that has a proximal end portion fixed to the installation portion and a distal end portion that can transmit the bias force to the specimen component test pieces stored in the test piece magazine.

It is preferable that, in the magazine holder according to the present invention, the framed casing includes a locking member that holds the test piece magazine guided to the storage space and, if engagement by the locking member is released, the test piece magazine is extruded out of the storage space under a resilient force of the torsion spring.

A test piece attachment apparatus according to the present invention is operable to attach a specimen component test piece to a portable specimen analyzer that has a distal end portion configured into a test piece holding portion for holding the specimen component test piece. The test piece attachment apparatus includes a test piece magazine having an inner space storing a plurality of specimen component test pieces aligned in a predetermined direction and a feed outlet via which the specimen component test pieces can be successively extruded; a magazine holder holding the test piece magazine in an exchangeable manner; a test piece urging member generating a bias force to press the specimen component test pieces aligned in the test piece magazine toward the feed outlet; and an extrusion mechanism capable of adjusting the position of the feed outlet to accord with the position of the test piece holding portion of the portable specimen analyzer and extruding one specimen component test piece positioned at the feed outlet to the test piece holding portion. The extrusion mechanism includes a guide casing that allows the magazine holder to move in an extrusion direction of the specimen component test piece positioned at the feed outlet; and an extrusion portion provided on the guide casing at a position where the extrusion portion can push the specimen component test piece positioned at the feed outlet of the test piece magazine and can extrude the specimen component test piece positioned at the feed outlet out of the test piece magazine in accordance with a movement of the magazine holder.

It is preferable that, in the test piece attachment apparatus according to the present invention, the magazine holder includes a distal end guide portion into which a distal end portion of the portable specimen analyzer can be inserted, and a positional relationship between the feed outlet of the specimen component test piece and the distal end guide portion is determined such that the specimen component test piece extruded from the feed outlet can be received by the test piece holding portion when the distal end portion of the portable specimen analyzer is inserted into the distal end guide portion.

It is preferable that, in the test piece attachment apparatus according to the present invention, the guide casing guides the magazine holder between an extruded position where the specimen component test piece can be pushed by the extrusion portion and an ordinary position where the specimen component test piece does not contact with the extrusion portion.

It is preferable that, in the test piece attachment apparatus according to the present invention, the guide casing has a cylindrical body capable of holding an outer surface of the magazine holder and allowing the magazine holder to slide in the longitudinal direction, with an engaging portion provided at an upper portion of the cylindrical body for holding the magazine holder at the ordinary position and a stopper portion provided at a lower portion of the cylindrical body for holding the magazine holder at the extruded position.

It is preferable that, in the test piece attachment apparatus according to the present invention, the extrusion mechanism includes a holder urging member that presses the magazine holder from the extruded position toward the ordinary position.

A test piece attachment apparatus according to the present invention may be used to attach a specimen component test piece to a portable specimen analyzer that has a distal end portion configured into a test piece holding portion for holding the specimen component test piece. The test piece attachment apparatus includes a test piece magazine having an inner space storing a plurality of specimen component test pieces aligned in a predetermined direction and a feed outlet via which the specimen component test pieces can be successively extruded; a magazine holder exchangeably holding the test piece magazine; a test piece urging member generating a bias force to press the specimen component test pieces aligned in the test piece magazine toward the feed outlet; a distal end guide portion provided on the magazine holder into which a distal end portion of the portable specimen analyzer can be inserted, and a positional relationship between the feed outlet of the specimen component test piece and the distal end guide portion is determined such that the specimen component test piece extruded from the feed outlet can be received by the test piece holding portion when the distal end portion of the portable specimen analyzer is inserted into the distal end guide portion; and an extrusion mechanism capable of adjusting the position of the feed outlet to accord with the position of the test piece holding portion of the portable specimen analyzer and extruding one specimen component test piece positioned at the feed outlet to the test piece holding portion. The extrusion mechanism includes a guide casing that allows the magazine holder to move in an extrusion direction of the specimen component test piece positioned at the feed outlet and guides the magazine holder between an extruded position where the specimen component test piece can be pushed by the extrusion portion and an ordinary position where the specimen component test piece does not contact with the extrusion portion; the extrusion portion provided on the guide casing at a position where the extrusion portion can push the specimen component test piece positioned at the feed outlet of the test piece magazine and can extrude the specimen component test piece positioned at the feed outlet out of the test piece magazine in accordance with a movement of the magazine holder; and a holder urging member that presses the magazine holder from the extruded position toward the ordinary position. The extrusion portion extrudes one specimen component test piece out of the test piece magazine via the feed outlet and sends the extruded test piece to the test piece holding portion of the portable analyzer when a user inserts the distal end portion of the portable specimen analyzer into the distal end guide portion of the magazine holder in the ordinary position and pushes the portable analyzer against the distal end guide portion such that the magazine holder reaches the extruded position.

In the above-described arrangements, a test piece magazine can store a plurality of specimen component test pieces aligned in a predetermined direction under an external bias force and extrude a specimen component test piece via a feed outlet under an external extrusion force. As the test piece magazine can store a plurality of specimen component test pieces, a user can easily attach a specimen component test piece to a portable specimen analyzer using the test piece magazine.

The boxlike casing may have an inner space capable of storing a plurality of specimen component test pieces, and an aperture from which a bias force is supplied. In this manner, a bias force generating element is not provided in the inner space of the boxlike casing. The storage efficiency of the specimen component test pieces can be improved.

The boxlike casing has a test piece outlet via which a foremost specimen component test piece can be extruded in an up-and-down direction and a slit with a uniform width for supplying an extrusion force to extrude the specimen component test piece upward. The slit has an extrusion length as an aperture length in the thickness direction of the specimen component test piece. The extrusion length is equivalent to the sum of the thickness of the front side surface portion of the boxlike casing and the thickness of the specimen component test piece. Thus, an external extrusion force can be applied to the specimen component test piece using an extrusion surface wider than a cross section of the specimen component test piece. The extrusion member can be enlarged to increase the strength.

The length of the inner space of the boxlike casing in an alignment direction of the specimen component test pieces is equivalent to the sum of the thickness of the biasing plate and a maximum length of aligned specimen component test pieces storable in the boxlike casing. Therefore, the storage efficiency of the specimen component test pieces can be increased to a level near a theoretical limit.

The biasing plate may be disposed in the inner space of the boxlike casing. Accordingly, the biasing plate can surely receive the bias force and transmit the bias force to the specimen component test pieces.

The biasing plate may have an outer shape and dimensions similar to those of the specimen component test piece, such that the biasing plate can be extruded via the feed outlet when the external extrusion force is applied to the biasing plate. Therefore, a user can know the timing the test piece magazine has been completely used and should be exchanged.

A marking is provided on a rearmost specimen component test piece which is finally extruded. Thus, a user can discriminate the rearmost specimen component test piece from other specimen component test pieces and can know the timing the test piece magazine has been completely used and should be exchanged.

In the above-described arrangements, a magazine holder may be configured to exchangeably hold a test piece magazine that can store a plurality of specimen component test pieces aligned in a predetermined direction under an external bias force. As the magazine holder can exchangeably hold a test piece magazine, a user can easily attach a specimen component test piece to a portable specimen analyzer using the magazine holder.

The magazine holder may include a framed casing that guides and supports the test piece magazine, an urging member that presses the specimen component test pieces stored in the test piece magazine in a predetermined direction, and an installation portion provided on the framed casing for mounting the urging member. In this manner, by integrating a portion storing the test piece magazine and the installation portion of the urging member, an overall size of the magazine holder including the test piece magazine and the urging member can be downsized.

The urging member may be a torsion spring that has a proximal end portion fixed to the installation portion and a distal end portion that can transmit the bias force to the specimen component test pieces stored in the test piece magazine. For example, compared to a coil spring, an overall size of the magazine holder including the test piece magazine and the urging member can be downsized.

The framed casing may include a locking member and, if engagement by the locking member is released, the test piece magazine is extruded out of the storage space under a resilient force of the torsion spring. Thus, a user can easily remove the test piece magazine.

In the above-described arrangements, the test piece attachment apparatus may include a test piece magazine having an inner space storing a plurality of specimen component test pieces and a feed outlet via which the specimen component test pieces can be successively extruded, a magazine holder exchangeably holding the test piece magazine, a test piece urging member generating a bias force to press the specimen component test pieces toward the feed outlet, and an extrusion mechanism capable of extruding one specimen component test piece positioned at the feed outlet to the test piece holding portion. The extrusion mechanism enables a user to easily attach a specimen component test piece to the test piece holding portion of the portable specimen analyzer.

Furthermore, a distal end guide portion may be provided on the magazine holder into which a distal end portion of the portable specimen analyzer can be inserted. The positional relationship between the feed outlet of the specimen component test piece and the distal end guide portion is determined such that the specimen component test piece extruded from the feed outlet can be received by the test piece holding portion when the distal end portion of the portable specimen analyzer is inserted into the distal end guide portion. Accordingly, when a user inserts the distal end portion of the portable specimen analyzer into distal end guide portion of the magazine holder, a specimen component test piece can be easily attached to the test piece holding portion of the portable specimen analyzer owing to the function of the extrusion mechanism.

Furthermore, an engaging portion may hold the magazine holder at an ordinary position and a stopper portion hold the magazine holder at an extruded position. Thus, the magazine holder can be surely moved from the ordinary position to the extruded position.

As the holder urging member presses the magazine holder from the extruded position to the ordinary position, the magazine holder is required to move against the urging force in the process of shifting from the ordinary position to the extruded position. On the other hand, after a specimen component test piece is extruded, the magazine holder can smoothly return to the ordinary position. In other words, no special operation is required to return the magazine holder to the ordinary position.

Moreover, the extrusion portion extrudes one specimen component test piece out of the test piece magazine via the feed outlet and sends the extruded test piece to the test piece holding portion of the portable analyzer, when a user inserts the distal end portion of the portable specimen analyzer into the distal end guide portion of the magazine holder in the ordinary position and pushes the portable analyzer against the distal end guide portion such that the magazine holder reaches the extruded position. Therefore, a user can attach a specimen component test piece to the test piece holding portion of the portable analyzer with a simple (one-touch) operation.

BRIEF DESCRIPTION OF THE DRAWINGS

The accompanying drawings, which are incorporated in and constitute a part of the specification, illustrate an embodiment of the invention and, together with the description, serve to explain the principles of the invention, in which.

DESCRIPTION OF PREFERRED EMBODIMENTS

Hereinafter, exemplary embodiments of the present invention are described in details with reference to the drawings. In the following description, an exemplary portable specimen analyzer is a portable urine analyzer that uses a test piece magazine applicable for the analysis of urine. If a specimen is other than urine, a specimen component test piece corresponding to the specimen can be selected and the selected test piece can be attached to a portable specimen analyzer.

For example, any of a PH test piece, a semi-quantitative ion test piece, an analytical test piece, or a temporary water quality test piece can be attached to the portable specimen analyzer. Examples of semi-quantitative ion test pieces includes a nitrite ion test piece usable for the detection of nitrite concentration in a food additive, a nitrate ion test piece usable for the detection of nitrate nitrogen concentration in a soil sample, a metallic ion test piece (an aluminum ion test piece, a copper ion test piece, a nickel ion test piece, etc) usable for the detection of metallic ion concentration in drinking water or industrial effluent, and an ascorbic acid ion test piece usable for the detection of vitamin C concentration in fruit juice.

Examples of analytical test pieces include a zinc test piece usable for the analysis of zinc component, a chlorine test piece usable for the analysis of residual chlorine, a tin test piece usable for the analysis of tin component, and a chromium (VI) compound test piece usable for the analysis of chromium (VI) compound component.

Furthermore, industrial effluent or other liquid-state specimen can be directly poured on a specimen component test piece attached to a portable specimen analyzer. Furthermore, if a test object is a component contained in a soil, it is preferable that the soil (i.e., test object) is first dried and then sufficiently stirred in refined water and filtered appropriately before obtaining a solubilized fluid specimen.

Furthermore, the method for subjecting a specimen component test piece to a specimen is not limited to directly pouring the specimen on a specimen component test piece. For example, it is preferable to collect a fluid specimen (e.g., industrial effluent) in a container and soak a specimen component test piece attached on a portable specimen analyzer into the specimen collected in the container.

Figure 1:
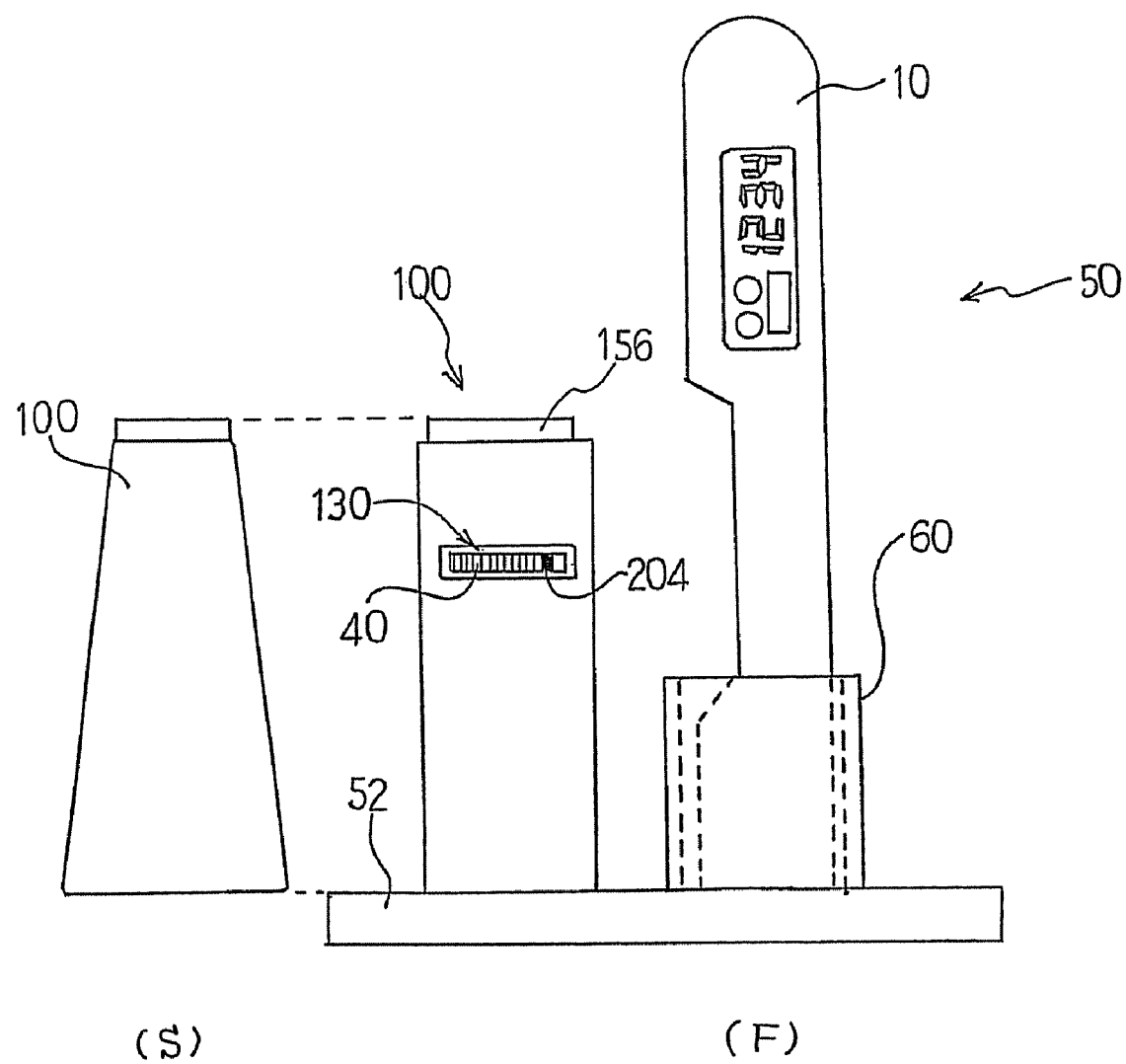
FIG. 1 illustrates a test piece attachment apparatus according to an embodiment of the present invention.

FIG. 1 consists of two drawings, a front view (F) and a side view (S), illustrating an exemplary test piece attachment apparatus 50. The front view (F) illustrates an overall arrangement of the test piece attachment apparatus 50. The test piece attachment apparatus 50 includes a device holder 60 and a test piece feeder 100 which are disposed on a pedestal 52. The device holder 60 is a cylindrical member that can hold a portable specimen analyzer 10 in an upright state. The test piece feeder 100 is a device enabling a user to perform a one-touch operation for feeding a specimen component test piece 40 to the portable specimen analyzer 10. The side view (S) illustrates a left side surface of the test piece feeder 100. The specimen component test piece 40 and the portable specimen analyzer 10 are independent members which are separable from the test piece attachment apparatus 50.

A detailed arrangement of the test piece feeder 100 is described later. An exemplary test piece holding portion of the portable specimen analyzer 10, especially a test piece attachment mechanism, is described later. A detailed arrangement of the specimen component test piece 40 is described later.

The pedestal 52 may be a base or a board on which the device holder 60 and the test piece feeder 100 are disposed and fixed. For example, the pedestal 52 may be a plastic plate having an appropriate thickness. The device holder 60 is a cylindrical member having an aperture larger than an outer shape of the portable specimen analyzer 10. When not using the portable specimen analyzer 10, the user can insert a distal end portion of the portable specimen analyzer 10 into the device holder 60 via the aperture so that the apparatus body of the portable specimen analyzer 10 can be held in an upright state. In general, a user pours a liquid-state specimen on the portable specimen analyzer 10 and then cleans the analyzer 10 with water. Therefore, the distal end portion of portable specimen analyzer 10 may be wet. The device holder 60 can hold the portable specimen analyzer 10 until the wet distal end portion of the portable specimen analyzer 10 is completely dried.

The test piece feeder 100 has a built-in magazine holder that can detachably hold a test piece magazine. The test piece magazine can accommodate a plurality of specimen component test pieces 40. The test piece feeder 100 is operable to successively extrude one specimen component test piece 40 from the magazine holder and send the extruded test piece 40 to the portable specimen analyzer 10. To realize the above-described test piece feeding operation, a user can simply push the portable specimen analyzer 10 into the test piece feeder 100. That is, a user can insert the portable specimen analyzer 10 to a distal-edge guide portion 156 provided on a distal end of the test piece feeder 100. If a user pushes the portable specimen analyzer 10 in this state, the test piece feeder 100 feeds one specimen component test piece 40 to the test piece holding portion of the portable specimen analyzer 10 from the test piece magazine.

The test piece feeder 100 has an inspection window 130 that enables a user to confirm unused specimen component test pieces 40 remaining in the test piece magazine. As understood from FIG. 1, a biasing plate 204 presses the specimen component test pieces 40 which are aligned in a predetermined direction. A user can visually check, through the inspection window 130, the position of the biasing plate 204 and the specimen component test pieces 40 remaining in a transparent body of the test piece magazine. The biasing plate 204 has a special color so that a user can easily identify the position of the biasing plate 204.

Figure 2:
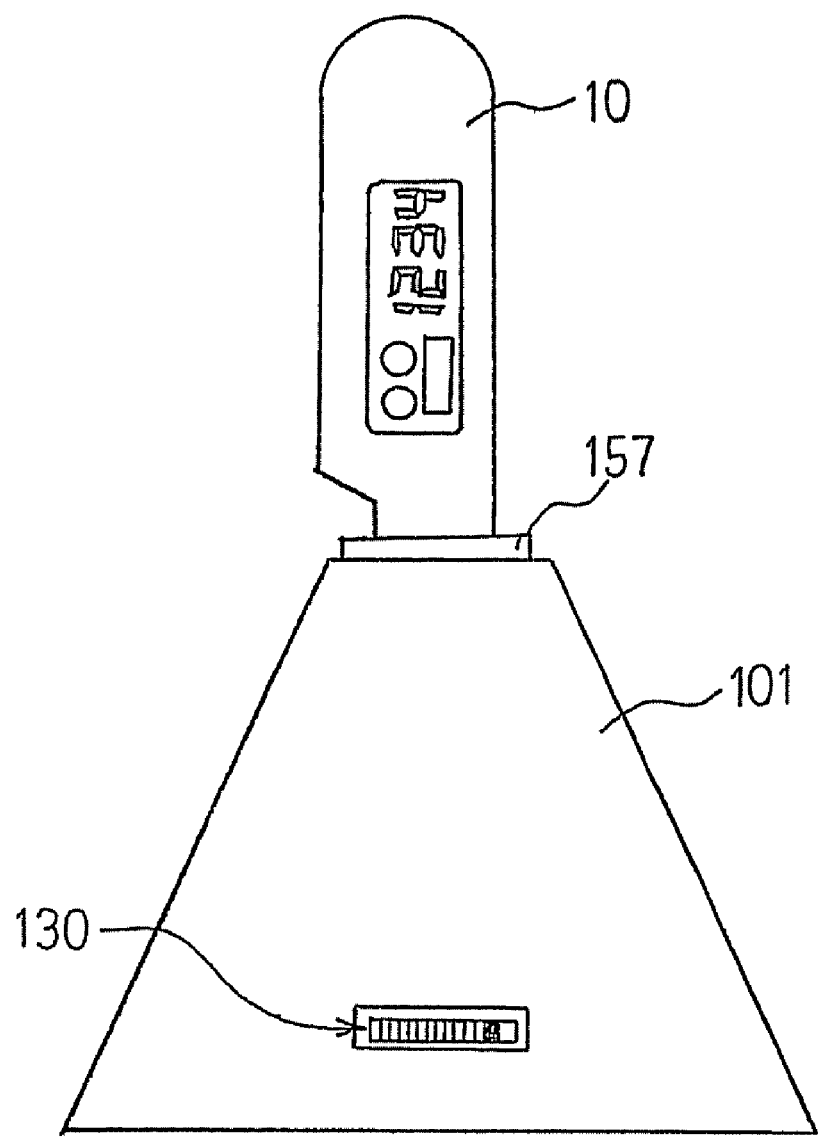
FIG. 2 illustrates a test piece attachment apparatus according to another embodiment of the present invention.

FIG. 2 illustrates another test piece feeder 101. The test piece feeder 101 is equivalent to a device integrating the test piece feeder 100, the device holder 60, and the pedestal 52 illustrated in FIG. 1. A test piece feeding arrangement of the test piece feeder 101 is similar to that of the test piece feeder 100 illustrated in FIG. 1. The test piece feeder 101 includes an analyzer guide portion 157 that has a sufficient depth for receiving and holding the portable specimen analyzer 10 in the upright state. When not using the portable specimen analyzer 10, the user can insert the portable specimen analyzer 10 into the analyzer guide portion 157. For example, the portable specimen analyzer 10 can be temporarily stored in the analyzer guide portion 157 to allow the distal end portion dry sufficiently.

When a user wishes to use the portable specimen analyzer 10, the user can push the portable specimen analyzer 10 downward (i.e., toward the bottom of the test piece feeder 101) from the inserted state. The test piece feeder 101 feeds one specimen component test piece 40 to the test piece holding portion of the portable specimen analyzer 10.

Figure 3:
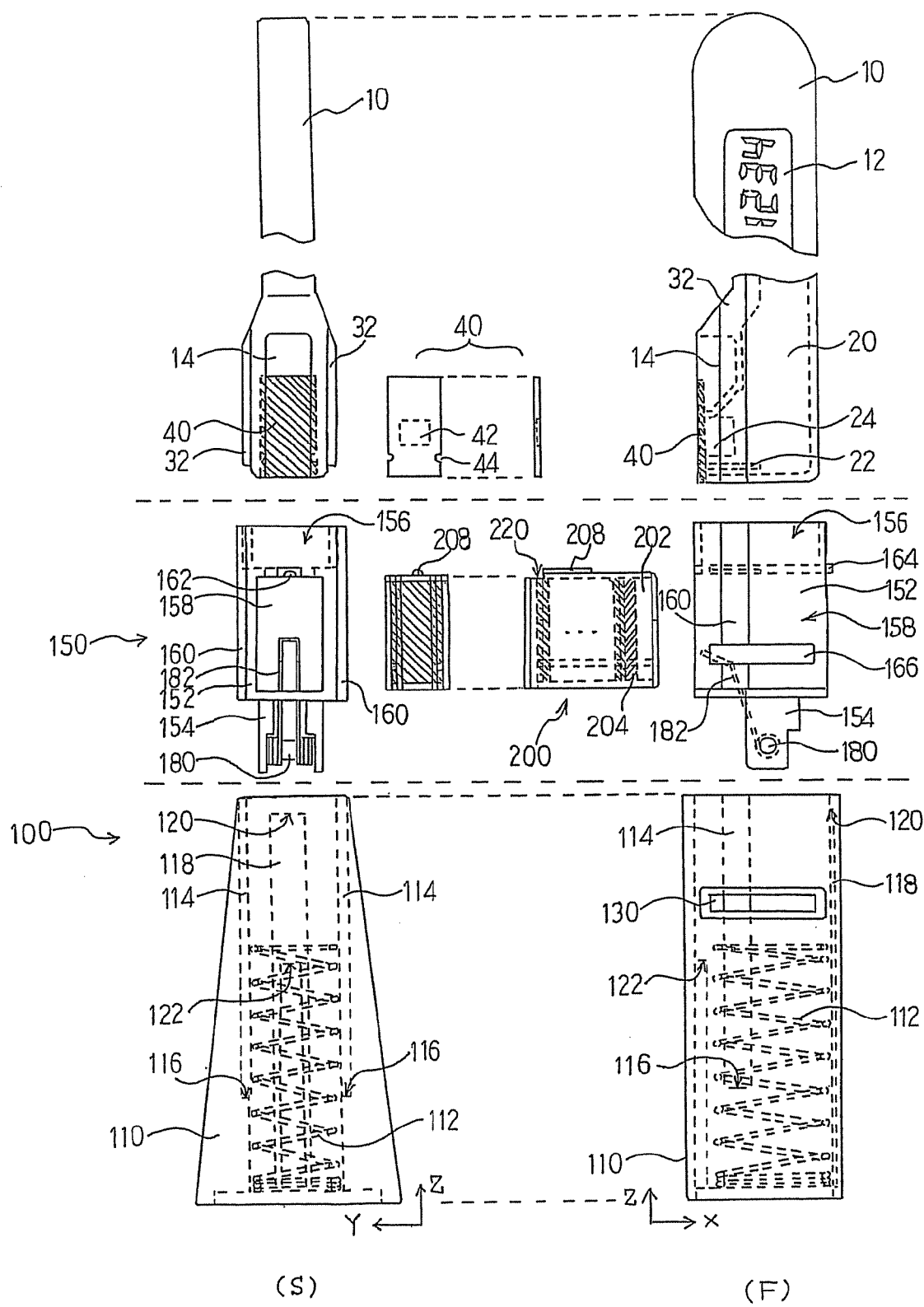
FIG. 3 illustrates components of the test piece attachment apparatus according to an embodiment of the present invention, which constitutes a test piece feeding mechanism.

FIG. 3 illustrates constituent members relating to the test piece feeding mechanism, including a left side view (S) and a front view (F). The front view (F) of FIG. 3 and the front view (F) of FIG. 1 are similar views seen from the same direction (i.e., the Y direction). More specifically, the front view (F) is on an XZ plane, while the side view (S) is on an YZ plane. In the configuration shown in FIG. 3, the portable specimen analyzer 10, a test piece magazine 200, a magazine holder 150 holding the test piece magazine 200, and a cylindrical casing 110 including a built-in extrusion mechanism are disposed, in that order, from the top to the bottom. The cylindrical casing 110, the magazine holder 150, and the test piece magazine 200 constitute the test piece feeder 100.

The portable specimen analyzer 10 is an object to which the test piece feeder 100 feeds a specimen component test piece 40. In other words, the portable specimen analyzer 10 is not a constituent member of the test piece feeder 100. However, as described above, the push operation of the portable specimen analyzer 10 causes the test piece feeder 100 to perform an operation for feeding the specimen component test piece 40. Thus, the portable specimen analyzer 10 is closely related to the test piece feeder 100 in structure and function The cylindrical casing 110 of the test piece feeder 100 can function as a guide casing capable of guiding the magazine holder 150 along an axial direction of the test piece feeder 100. Furthermore, the cylindrical casing 110 is capable of pushing specimen component test piece 40 out of the test piece magazine 200 in response to a movement of the magazine holder 150. The latter function of the cylindrical casing 110 corresponds to a test piece extrusion mechanism.

The cylindrical casing 110 has a truncated rectangular conical body with an inner hollow space. The wall defining the inner hollow space is capable of guiding the magazine holder 150. Furthermore, three guide grooves formed on the wall can prevent the magazine holder 150 from rotating while allowing the magazine holder 150 to move in the axial direction. Furthermore, as an extrusion portion having an extrusion function, an extrusion projection 122 is provided at a position corresponding to a feed port 220 of the test piece magazine 200 held in the magazine holder 150.

Furthermore, a coil spring 112 having a lower end fixed to the cylindrical casing 110 is provided in the inner hollow space of the cylindrical casing 110. The coil spring 112 is an urging member that can press the magazine holder 150 upward. Two of the above-described guide grooves are grooves 114 that can mate with ridges 160 extending on an outer surface of the magazine holder 150 in the up-and-down direction. Each groove 114 extends downward from an upper aperture of the cylindrical casing 110 in the axial direction of the cylindrical casing 110. The groove 114 has a lower-limit end 116. The lower-limit end 116 regulates the lowermost position of the magazine holder 150 moving in the axial direction of the cylindrical casing 110.

In this respect, the lower-limit end 116 is a stopper of the magazine holder 150. The rest of the above-described guide grooves is a groove 118 whose position accords with the position of a stopper projection 164 provided on the outer surface of the magazine holder 150. The groove 118 has an upper-limit edge 120 at a position slightly offset from the periphery of the upper aperture of the cylindrical casing 110. The groove 118 extends downward in the axial direction of the cylindrical casing 110. The upper-limit edge 120 is an engaging portion that can regulate an uppermost position of the magazine holder 150 when the magazine holder 150 moves in the axial direction of the cylindrical casing 110.

The outer shape of the magazine holder 150 including the stopper projection 164 is slightly larger than the inner hollow space of the cylindrical casing 110. Namely, the dimensions of the magazine holder 150 do not allow a user to insert the magazine holder 150 into the cylindrical casing 110 from the upper aperture. However, the cylindrical casing 110 and the magazine holder 150 are elastic enough to enable a user to insert the magazine holder 150 into the cylindrical casing 110 from the upper aperture and push the magazine holder 150 downward so that the stopper projection 164 can engage with the groove 118.

In this case, an upper end of the coil spring 112 provided in the cylindrical casing 110 resiliently supports a bottom surface of the magazine holder 150. Thus, the magazine holder 150 is stably held at a predetermined position where the stopper projection 164 abuts the upper-limit edge 120 of the groove 118 with a resilient force acting upward. This position can be referred to as the "ordinary position" because the extrusion projection 122 (having the extrusion function) does not contact or interfere with the magazine holder 150. In other words, the upper-limit edge 120 of the groove 118 can regulate the ordinary position of the magazine holder 150.

If a user pushes the magazine holder 150 down in the axial direction of the cylindrical casing 110, the extrusion projection 122 interferes or contacts with the magazine holder 150 and pushes one specimen component test piece 40 upward from the test piece magazine 200 as described later. Then, if the magazine holder 150 reaches the lower-limit end 116 of the groove 114, one specimen component test piece 40 can be completely pushed out of the test piece magazine 200. The position of the lower-limit end 116 and the position of the extrusion projection 122 are determined beforehand so as to satisfy the above-described relationship. Accordingly, the position where the magazine holder 150 reaches the lower-limit end 116 is an extrusion position where the specimen component test piece 40 is pushed out.

As described above, the coil spring 112 of the cylindrical casing 110, the lower-limit end 116 of the groove 114, and the upper-limit edge 120 of the groove 118 can cooperatively function as a guide mechanism that allows the magazine holder 150 to move between the ordinary position and the extrusion position. The extrusion projection 122 is capable of extruding one specimen component test piece 40 out of the magazine holder 150 in response to a movement of the magazine holder 150.

Figure 4:
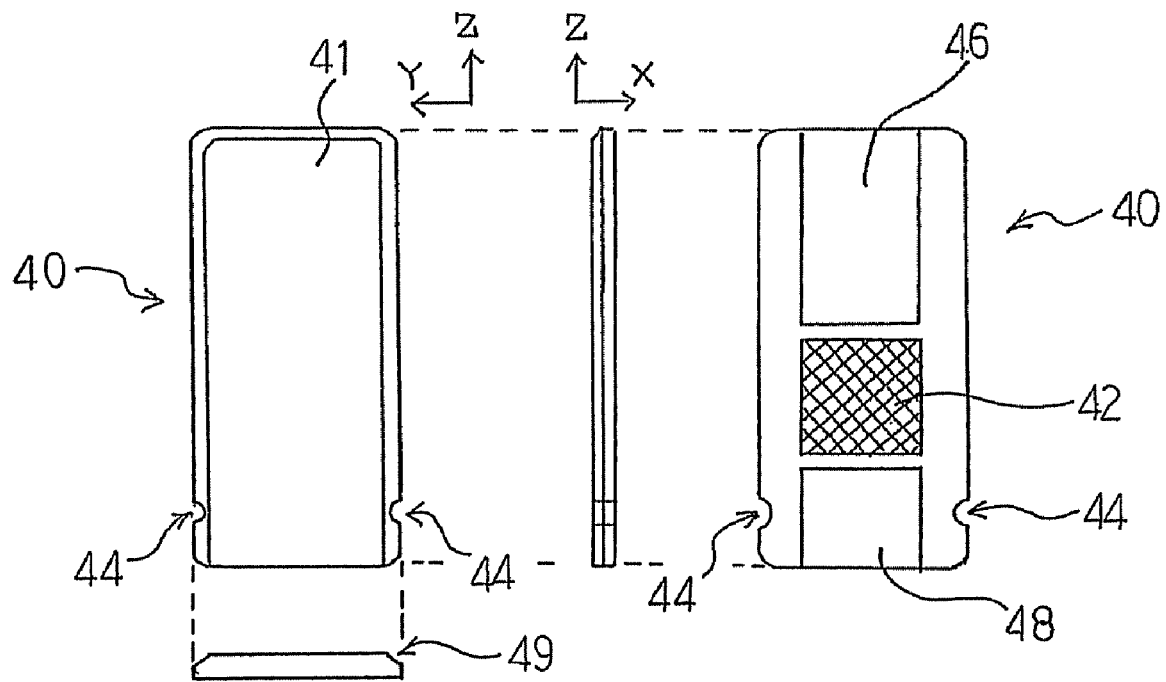
FIG. 4 consists of four drawings illustrating a specimen component test piece according to an embodiment of the present invention.
Figure 5:
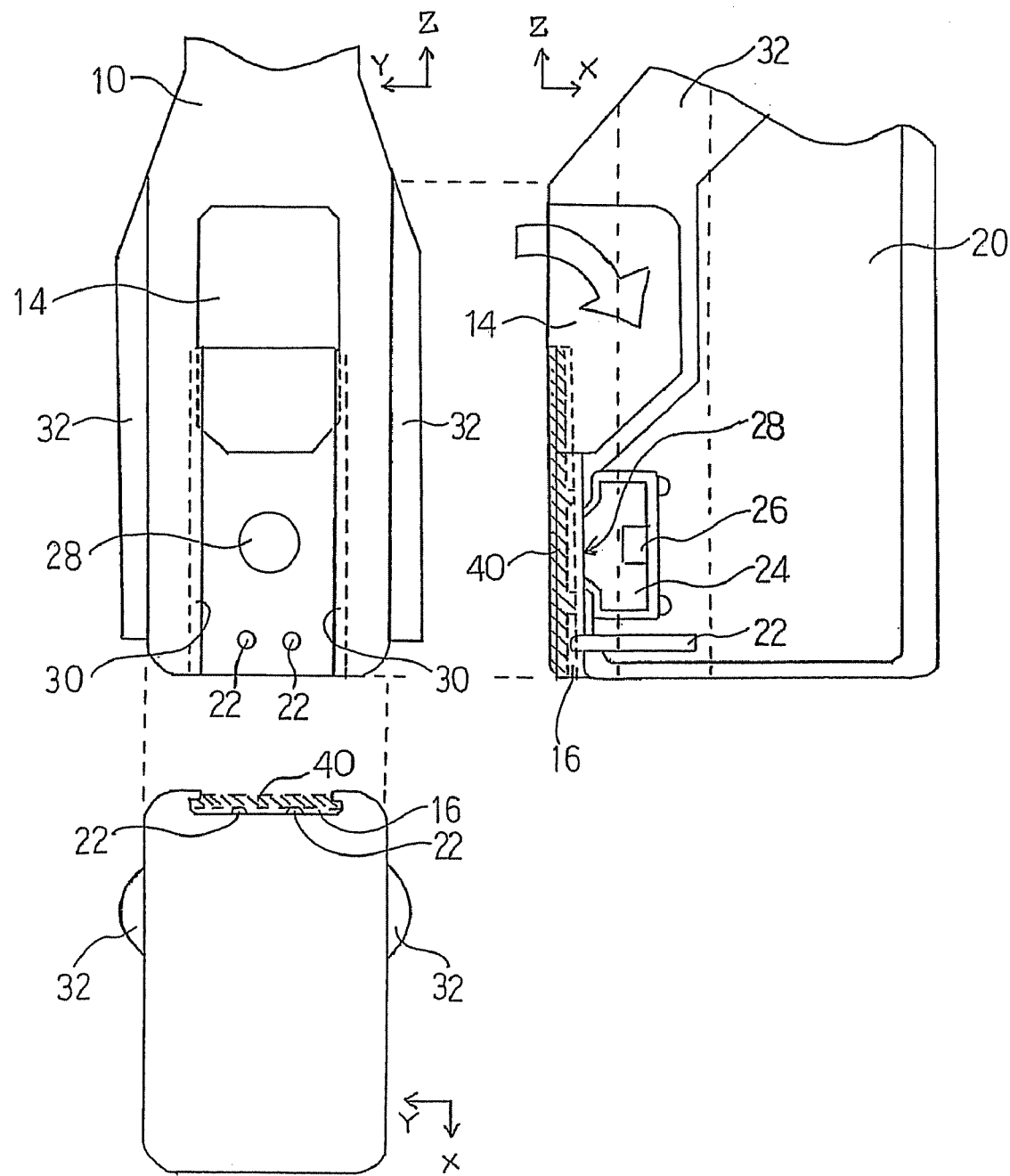
FIG. 5 consists of three drawings illustrating a test piece feeding mechanism of a portable specimen analyzer according to an embodiment of the present invention.
Figure 6:
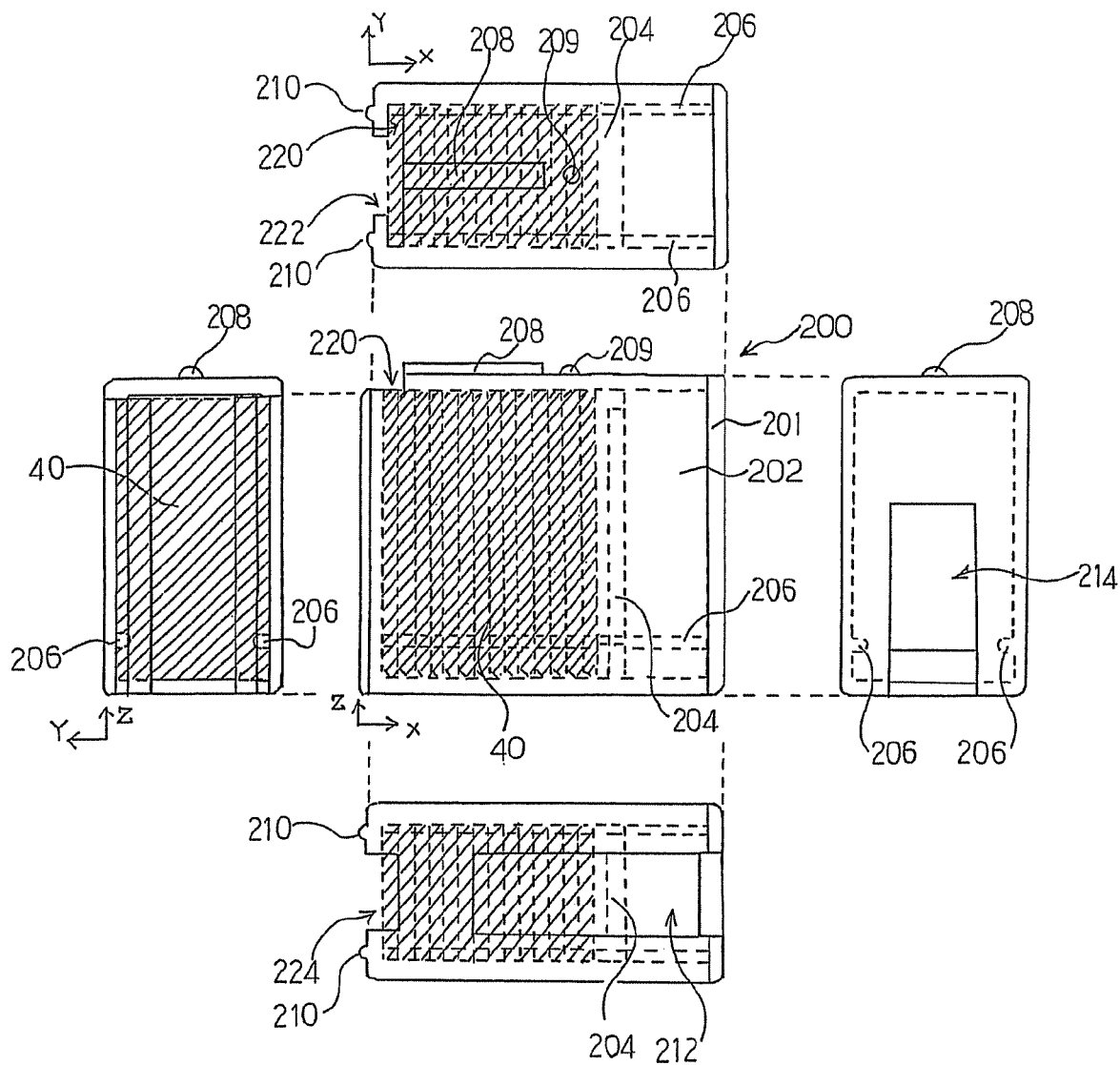
FIG. 6 consists of five drawings illustrating a test piece magazine according to an embodiment of the present invention.

FIGS. 4, 5, 6, and 8 illustrate details of constituent members other than the cylindrical casing 110. More specifically, FIG. 4 consists of four drawings illustrating the specimen component test piece 40 stored in the test piece magazine 200; FIG. 5 consists of three drawings illustrating a portion relating to the test piece feeding mechanism of the portable specimen analyzer 10; FIG. 6 consists of five drawings illustrating the test piece magazine 200; and FIG. 8 consists of four drawings illustrating the magazine holder 150.

The specimen component test piece 40 is a sticklike member that holds a test patch which absorbs urine and changes color. A base material of the "test piece" is, for example, made of a paper material selectable from various types of papers, a plastic sheet or a plastic thin plate, or a metallic thin plate that can hold a test patch. FIG. 4 illustrates four sides of the specimen component test piece 40.

The specimen component test piece 40 includes a plastic base 41 and a test patch 42 affixed on a surface of the base. The test patch 42 absorbs a liquid-state specimen and changes color. The test patch 42 contains a reagent which is determined according to a component of urine to be detected. For example, a reagent of the test patch 42 can be selected according to each detection object (e.g., urine sugar, protein, occult blood, urinary urobilinogen, ketone body, bilirubin, nitrite, or leukocyte).

Furthermore, if the test patch 42 includes a reagent capable of detecting human chorionic gonadotropin contained in the urine, a pregnancy reaction can be detected based on a coloring reaction of the test patch 42. Although FIG. 4 illustrates only one test patch 42, a specimen component test piece may include two or more test patches adhered on the base so that the portable specimen analyzer can simultaneously analyze color changes of a plurality kinds of test patches.

The base 41 of the specimen component test piece 40 is a black plastic plate which has sufficient light-shielding properties. The base 41 need only be only partially opaque (e.g., may have only one black face), as long is it can sufficiently shield the test patch 42 from external light. The specimen component test piece 40 has a flat rectangular shape. The test patch 42 is positioned between two shallow recesses 46 and 48 formed on the base 41. The recess 46 is positioned at an upstream side of the test patch 42, while the recess 48 is positioned at a downstream side of the test patch 42. The upstream side and the downstream side of the test patch 42 correspond to an upstream side and a downstream side of the portable specimen analyzer 10 through which urine flows from a urine gathering bath toward the test patch 42. Accordingly, the recess 46 can guide urine to smoothly flow into the test patch 42. The recess 48 can guide urine to smoothly flow out of the test patch 42.

The base 41 of the specimen component test piece 40 has an outer periphery configured into a taper surface 49. The taper surface 49 is capable of guiding the specimen component test piece 40 to be smoothly inserted into and held at the test piece holding portion of the portable specimen analyzer 10. The specimen component test piece 40 has a pair of recesses 44 at both sides of the base 41. The recesses 44 can support a plurality of specimen component test pieces 40 aligned and stored in the test piece magazine 200. More specifically, a pair of protruding guides is provided on an inner wall of the test piece magazine 200 so as to correspond to respective recesses 44. Thus, the protruding guides can hold the recesses 44 of the specimen component test pieces 40 aligned in the test piece magazine 200. The specimen component test pieces 40 can successively move along the protruding guides.

For example, the specimen component test piece 40 may be a rectangular board of approximately 19 mm×approximately 9 mm with a thickness of approximately 1 mm. The test patch 42 has a square shape of approximately 5 mm×approximately 5 mm. The dimensions of each specimen component test piece 40 can be appropriately determined according to the intended use or the shape of the portable specimen analyzer 10.

FIG. 5 illustrates the distal end portion of the portable specimen analyzer 10, i.e., a portion where the specimen component test piece 40 is attached to absorb urine. Among three drawings in FIG. 5, the drawing on the XZ-plane (corresponding to a front view) is a cross-sectional view as seen from the front of the device.

The portable specimen analyzer 10 has a specimen gathering bath 14 provided at the distal end portion thereof. In FIG. 5, the large arrow marking indicates urine to be subjected to a specimen analysis which is poured into the specimen gathering bath 14. Furthermore, the portable specimen analyzer 10 has a test piece holding portion 30 provided at the more distal end portion from the specimen gathering bath 14. The test piece holding portion 30 can hold the specimen component test piece 40. The test piece holding portion 30 includes a pair of guide grooves configured to engage with the taper surface 49 formed along the periphery of the specimen component test piece 40 as illustrated in FIG. 4. The test piece holding portion 30 can support the specimen component test piece 40 in a state wherein the test patch 42 adhered thereon can face the portable specimen analyzer 10.

The distal end portion of the portable specimen analyzer 10 includes an electronic component storage region 20 and a water proof wall that separates the electronic component storage region 20 from the specimen gathering bath 14. The electronic component storage region 20 includes a sensing portion 24. The sensing portion 24 includes a light emitting/receiving element 26 and a detection window 28 that allows light to pass through. An appropriate positional setting of the test piece holding portion 30 enables the test patch 42 to just face the detection window 28 in a state wherein the specimen component test piece 40 is held by the test piece holding portion 30. Furthermore, the positional setting of the test piece holding portion 30 can be optimized to position a pair of electrically-conductive terminals 22 in the downstream recess 48 illustrated in FIG. 4.

With the above-described positional relationship, in a state wherein the specimen component test piece 40 is held by the test piece holding portions 30, if urine is poured into the specimen gathering bath 14, the urine flows in a fluid channel between a face of the specimen component test piece 40 on which the test patch 42 is affixed and a face on which the detection window 28 is provided. This fluid channel is referred to as "specimen flow channel." If urine flows in the specimen flow channel and reaches the pair of electrically-conductive terminals 22, the resistance between two terminals 22 changes and a time the urine has been poured can be detected based on a resistance change. Furthermore, the light emitting/receiving element 26 can emit light from the sensing portion 24. The light emitting/receiving element 26 can receive reflection light from the test patch 42 that has changed color when it has absorbed the urine. Thus, the light emitting/receiving element 26 can measure a degree of color change. As described above, the urine detection and the test patch coloring measurement can be realized.

Furthermore, the distal end portion of the portable specimen analyzer 10 has a pair of guide ridges 32 configured into a swollen shape. The guide ridges 32 extend in the Y-direction on a front outer wall and a rear outer wall of the distal end portion of the portable specimen analyzer 10 when seen in a front view. The magazine holder 150 has the ridges 160 corresponding to the guide ridges 32. These members can function as a guide mechanism that inserts the distal end portion of the portable specimen analyzer 10 into the magazine holder 150.

The test piece magazine 200 illustrated in FIG. 6 is a casing that can store a plurality of specimen component test pieces 40 aligned in a predetermined direction. The test piece magazine 200 has a slit 222 at a position corresponding to the feed port 220. An external bias force is applied to the specimen component test pieces 40 which are aligned in a predetermined direction in the test piece magazine 200. A foremost specimen component test piece 40 placed in the slit 222 can be extruded from the feed port 220. According to the arrangement illustrated in FIG. 3, a later-described torsion spring 182 generates an external bias force. The extrusion projection 122 of the cylindrical casing 110 transmits an extrusion force (i.e., a reaction force) to the specimen component test piece 40 when the portable specimen analyzer 10 is pushed down relative to the test piece feeder 100.

The test piece magazine 200 is made of a transparent plastic material so that a user can visually confirm its contents. As described above, when the test piece magazine 200 is installed in the test piece feeder 100, a user can visually inspect the specimen component test pieces 40 remaining in the test piece magazine 200 via the inspection window 130 of the cylindrical casing 110 (refer to FIG. 1). In this case, only a limited portion corresponding to the inspection window 130 can be constituted by a transparent material and the other portion can be constituted by an opaque material.

The test piece magazine 200 has a boxlike casing 201 having a rectangular shape. The boxlike casing 201 has an internal space 202 that can accommodate a plurality of specimen component test pieces 40 and the biasing plate 204 pushing the test pieces 40 toward the feed port 220. A pair of projecting guides 206, each extending in the alignment direction of the test pieces 40, is formed on the inner wall of the internal space 202. The position of the projecting guides 206 accords with the position of the recesses 44 provided on the longitudinal sides of each specimen component test piece 40.

The projecting guides 206 can engage with the recesses 44 so that the plurality of specimen component test pieces 40 can be stably aligned in the thickness direction. The projecting guides 206 extend in the X direction illustrated in FIG. 6. Namely, the thickness of each test piece 40 is measured in the X direction and the length of the longer side(longitudinal direction) of each test piece 40 is measured in the Z direction in a state wherein the test pieces 40 are stored in the internal space 202 of the test piece magazine 200.

Regarding the front and rear faces of each test piece 40 according to the example illustrated in FIG. 5, the test patch 42 is provided on the front face of the specimen component test piece 40 in a state wherein the specimen component test piece 40 is attached to the test piece holding portion 30 of the portable specimen analyzer 10. The rear face of the specimen component test piece 40 is opposed to the feed port 220. Thus, as illustrated in (F) of FIG. 3, the position of the feed port 220 of the test piece magazine 200 accords with the position of the test piece holding portion 30 of the portable specimen analyzer 10.

According to the above-described arrangement, the specimen component test piece 40 can be extruded from the feed port 220 in the Z direction which accords with the axial direction of the cylindrical casing 110 (i.e., a moving direction of the magazine holder 150 which is guided by the cylindrical casing 110).

As described above, in addition to the specimen component test pieces 40, the biasing plate 204 is disposed in the internal space 202 of the test piece magazine 200. To transmit a bias force to the biasing plate 204, a distal end portion of the torsion spring 182 is placed in the internal space 202 of the test piece magazine 200. However, except for the specimen component test pieces 40 and the biasing plate 204, substantially no other member is disposed in the internal space 202. In other words, the internal space 202 of the test piece magazine 200 can be shared by the biasing plate 204 and the plurality of specimen component test pieces 40. More specifically, the length of the internal space 202 of the boxlike casing 201 in the alignment direction of the specimen component test pieces 40 (i.e., the X direction illustrated in FIG. 6) corresponds to a length defined by the following formula:

(maximum number of the specimen component test pieces 40 storable in the internal space 202)×(board thickness of the specimen component test piece 40)+(thickness of the biasing plate 204)

For example, if the board thickness of each specimen component test piece 40 is approximately 1 mm, the maximum number of the specimen component test pieces 40 storable in the internal space 202 is 18, and the thickness of the biasing plate 204 is approximately 2 mm., the length of the internal space 202 of the test piece magazine 200 in the X direction is 20 mm+$\alpha$ (=18×1 mm+2 mm+$\alpha$), where $\alpha$ is a tolerance or margin (e.g., $\alpha$=1 mm) which can be set considering the accuracy of measurement of respective members.

According to this example, the storage efficiency of the specimen component test pieces 40 relative to the internal space 202 is approximately 86% (=18/21) which is close to a theoretical storage efficiency 90% (=18/20). Thus, it is understood that the storage efficiency of the specimen component test pieces 40 is very high. As described above, a higher storage efficiency can be attained when the torsion spring 182 is used as an element for giving a resilient force to the biasing plate 204, because only the distal end portion of the torsion spring 182 is placed in the internal space 202 and therefore the internal space 202 can be shared by the biasing plate 204 and the specimen component test pieces 40.

The biasing plate 204 is a member disposed outside the plurality of specimen component test pieces 40. The biasing plate 204 presses the test pieces 40 toward the feed port 220. As described above, when the test piece magazine 200 is regarded as an independent unit, the biasing plate 204 is disposed in the internal space 202 of the boxlike casing 201. The biasing plate 204 has one surface which abuts the specimen component test pieces 40 aligned in the internal space 202. The other surface of the biasing plate 204 receives a bias force applied in the alignment direction of the specimen component test pieces 40. The resilient force (i.e., pressing force) can be generated by the torsion spring 182 of the magazine holder 150. If a pressing force is directly applied to the face of the specimen component test piece 40 on which the test patch 42 is provided, the test patch 42 may be damaged. For the reasons described above, the torsion spring 182 is arranged to press the specimen component test pieces 40 indirectly (i.e., via the biasing plate 204). In planar shape, the biasing plate 204 is substantially the same as the specimen component test pieces 40. The biasing plate 204 has recesses corresponding to the projecting guides 206.

Furthermore, as described with reference to FIG. 1, it is preferable that a marker is put on the biasing plate 204 (not the specimen component test piece 40) so that a user can visually inspect the specimen component test pieces 40 remaining in the internal space 202 via the inspection window 130. In summary, the biasing plate 204 can prevent the specimen component test pieces 40 from being damaged by the torsion spring 182 and can indicate the position of the last test piece 40. The biasing plate 204 can be made of an appropriate plastic material and has an appropriate shape.

Two cutout openings (windows) 212 and 214 are provided on a bottom surface and a left side surface (i.e., rear surface) of the test piece magazine 200. The torsion spring 182 of the magazine holder 150 can be placed in the cutout openings (windows) 212 and 214 to resiliently press the biasing plate 204. The torsion spring 182, generating a bias force, can press the specimen component test pieces 40 aligned in a predetermined direction. The cutout openings (windows) 212 and 214 can be referred to as "apertures" for supplying a bias force to the biasing plate 204.

Furthermore, a projecting guide 208 is formed on an upper surface of the test piece magazine 200. The projecting guide 208 functions as a guide when the test piece magazine 200 is installed on the magazine holder 150. The projecting guide 208 extends in the X direction. A groove 162, corresponding to the projecting guide 208, is provided on the magazine holder 150. The projecting guide 208 and the groove 162 can guide the test piece magazine 200 that slide (move) in the X direction relative to the magazine holder 150, for example, when a user attaches or detaches the magazine 200 which is exchanged.

Furthermore, the test piece magazine 200 has a lock projection 209 formed on the upper surface thereof, in addition to the projecting guide 208. When the test piece magazine 200 is installed on the magazine holder 150, the lock projection 209 fixes the position of the test piece magazine 200 relative to the magazine holder 150. The magazine holder 150 has a lock recess 163 corresponding to the lock projection 209. The projecting guide 208 and the groove 162 can guide the test piece magazine 200 which is installed on when the magazine holder 150. If a user further pushes the test piece magazine 200, the lock projection 209 engages with the lock recess 163 and accordingly the position of the test piece magazine 200 relative to the magazine holder 150 can be fixed. Furthermore, if a user pushes the test piece magazine 200 in the opposite direction, the lock projection 209 is disengaged from the lock recess 163 and therefore the test piece magazine 200 can be removed from the magazine holder 150.

In the test piece magazine 200, the slit 222 and the feed port 220 are provided at the side surface towards which the specimen component test pieces 40 are pressed by the biasing plate 204. In FIG. 6, the specimen component test pieces 40 are aligned in the X direction. The biasing plate 204 is positioned at the rightmost (i.e., +X side). The slit 222 and the feed port 220 are positioned at the left side of the test piece magazine 200 (i.e., the −X side).

The slit 222 is an aperture having a predetermined width and formed on the left side wall of the test piece magazine 200. The feed port 220, provided on the upper surface of the test piece magazine 200, is an aperture portion through which the specimen component test piece 40 can be extruded in the upper direction. Compared to the slit 222 formed on the left side wall of the test piece magazine 200, the feed port 220 is offset inward. The slit 222 has an aperture width narrower than the width of the feed port 220, as understood from the upper surface view of FIG. 6. The lower surface view of FIG. 6 illustrates a slit 224 (i.e., the lower end of the slit 222).

Accordingly, the foremost specimen component test piece 40 (i.e., the leftmost specimen component test piece 40) abuts a wall (i.e., an inside wall of the front surface side of the test piece magazine 200) having a width corresponding to a difference between the feed port 220 and the slit 222, in a state wherein the plurality of specimen component test pieces 40 are pressed by the biasing plate 204 toward the feed port 220. Namely, under the resilient force of the biasing plate 204, the foremost specimen component test piece 40 can be stably positioned at the leftmost side and face the feed port 220.

As described above, the feed port 220 is an aperture that enables a foremost specimen component test piece 40 (i.e., one of test pieces 40 aligned in the internal space 202 of the test piece magazine 200) to protrude out of the test piece magazine 200. The feed port 220, provided on the upper surface of the boxlike casing 201, has an aperture size sufficient for enabling a foremost one of the specimen component test pieces 40 aligned in the casing 201 to move in the up-and-down direction. Namely, the aperture width of the feed port 220 (i.e., an aperture width in the Y direction) is slightly larger than the width of the specimen component test piece 40. The length of the feed port 220 (i.e., an aperture thickness in the X direction) is slightly larger than the board thickness of the specimen component test piece 40.

The slit 222 (and 224) is an aperture having a uniform slit width and extending in the up-and-down direction on the front surface of the boxlike casing 201 towards which the specimen component test pieces 40 are pressed. The slit 222 (and slit 224) provides a space for supplying an extrusion force which is required to push the specimen component test piece 40 upward. More specifically, when the extrusion projection 122 of the cylindrical casing 110 moves along the slit 222 (and slit 224), an extrusion force is transmitted to the lower end portion of the specimen component test piece 40.

As apparent from the upper surface view and the lower surface view of FIG. 6, the slit 222 extends thoroughly in the Z direction on the left side surface of the test piece magazine 200. In other words, slit 222 extends over a full length of the front side surface portion from a lower surface portion of boxlike casing 201 to the upper surface of boxlike casing 201. The lower surface view of FIG. 6 illustrates the slit 224. On the lower surface of the boxlike casing 201, the aperture length of the slit 224 in the thickness direction of the specimen component test piece 40 is substantially equal to the sum of the thickness of the front wall portion of the boxlike casing 201 and the board thickness of the specimen component test piece 40.

Furthermore, on the upper surface of the boxlike casing 201, the slit 222 merges with the feed port 220. The aperture portion corresponding to the width of the slit 222 not only functions as the feed port 220 (i.e., part of the feed port 220) but also functions as the slit 222 (i.e., part of the slit 222). Accordingly, an aperture length of the slit 222 in the thickness direction of the specimen component test piece 40 is substantially equal to the length of the slit 224, i.e., ((the thickness of the front wall portion of the boxlike casing 201)+(the board thickness of the specimen component test piece 40)).

As described above, when the extrusion projection 122 of the cylindrical casing 110 moves along the slit 222 (and slit 224), an extrusion force is transmitted to the lower end portion of the specimen component test piece 40. The sum of the thickness of the front wall portion of the boxlike casing 201 and the board thickness of one specimen component test piece 40 can be referred to as the "extrusion length." An extrusion force can be supplied to the specimen component test piece 40 by relatively moving the extrusion projection 122 using a region of an extrusion surface defined by the extrusion length and the slit width.

As described above, the slit 222 (and 224) corresponds to the extrusion projection 122 of the cylindrical casing 110. Similar slits 172 and 176 are provided on the magazine holder 150. Accordingly, when the test piece magazine 200 installed on the magazine holder 150 causes a Z-directional movement in the cylindrical casing 110, the extrusion projection 122 can move in the slit 222 (and slit 224). Namely, if the magazine holder 150 is pushed downward in the cylindrical casing 110, the extrusion projection 122 moves upward in the slit 222 (and slit 224) of the test piece magazine 200 and can push the specimen component test piece 40 out of the test piece magazine 200.

Figure 7:
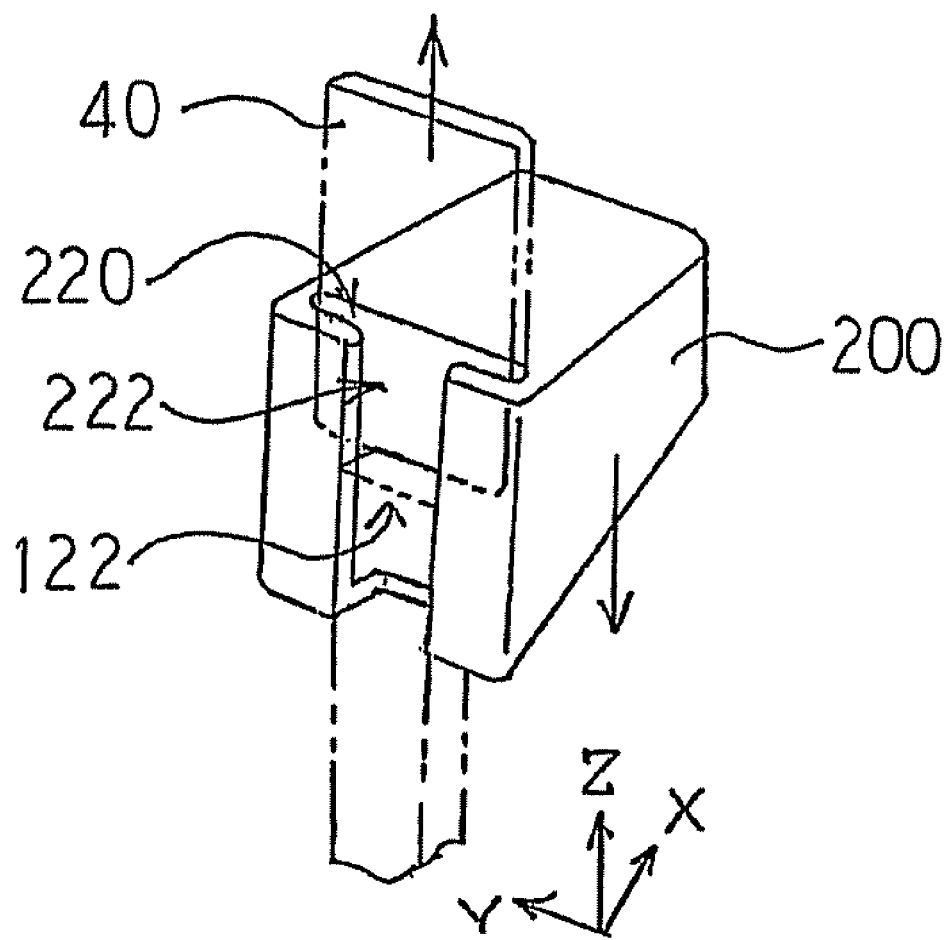
FIG. 7 illustrates extrusion of a specimen component test piece which is pushed out of the test piece magazine according to an embodiment of the present invention.

As illustrated in FIG. 7, if the test piece magazine 200 moves downward (i.e., in the −Z direction), the extrusion projection 122 pushes one specimen component test piece 40 located at the feed port 220 of the test piece magazine 200 upward (the +z direction). As illustrated in FIG. 7, provision of the slit 222 is effective to assure a sufficient thickness of the extrusion projection 122 in the X direction, compared to the board thickness of the specimen component test piece 40. Thus, the extrusion projection 122 possesses a sufficient strength for surely performing the above-described push-out operation.

Referring again to FIG. 6, on the left side wall of the test piece magazine 200, two slide projections 210 are formed at both sides of the slit 222 (and slit 224) on an outer wall surface. Each slide projection 210 extends in the Z direction. When the test piece magazine 200 installed on the magazine holder 150 causes a Z-directional movement in the cylindrical casing 110, the slide projections 210 can provide a small contact area between test piece magazine 200 and the inner surface of the cylindrical casing 110. In other words, the slide projections 210 can reduce a frictional force acting between test piece magazine 200 and the inner surface of the cylindrical casing 110.

As described above, the test piece magazine 200 is made of a transparent material. A plurality of specimen component test pieces 40 and a single biasing plate 204 can be stored in the internal space 202 of the boxlike casing 201. The specimen component test pieces 40 can be successively extruded from the feed port 220. However, the following modified configurations can also be used. For example, the biasing plate 204 can possess moisture absorption properties. In this case, the biasing plate 204 can be entirely or partly constituted by a moisture absorption member, such as, for example, a silica gel.

The biasing plate 204 may, for example, have an outer shape identical or similar to that of the specimen component test piece 40. In this case, similar to the specimen component test piece 40, the biasing plate 204 can be extruded from the feed outlet when an external extrusion force is applied. In this case, if the biasing plate 204 is extruded from the test piece magazine 200, a user can know when the test piece magazine 200 has been completely used and should be exchanged.

The biasing plate 204 may also be omitted. In such a case, a rearmost specimen component test piece (i.e., a specimen component test piece finally extruded) receives the bias force. Accordingly, it is preferable that the rearmost specimen component test piece is differentiated from other ordinary specimen component test pieces, so that the rearmost specimen component test piece cannot be used for the specimen component analysis. It is, however, obvious that the rearmost specimen component test piece can be used for the analysis, if it is usable.

Furthermore, the rearmost specimen component test piece may have marking which identifies the rearmost specimen component test piece and differentiates it from other ordinary specimen component test pieces. The biasing plate 204 may have similar marking. As described above, marking which discriminates the rearmost specimen component test piece from other ordinary specimen component test pieces enables a user to recognize when the final specimen component test piece has been extruded. For example, the marking may use a color other than black. Any color other than black can be used as a base color of the specimen component test piece, and examples of commonly-recognized colors indicating the timing of exchange may be red or pink. A color capable of intensifying the contrast to black is, for example, white.

Furthermore, the test piece magazine 200 may be made of an opaque material. In such a case, a user cannot visually verify the number (or volume) of specimen component test pieces 40 remaining in the magazine 200. Therefore, it is preferable to employ the above-described arrangement that the biasing plate is finally extruded or the rearmost specimen component test piece differentiated from other ordinary test pieces is finally extruded.

Figure 8:
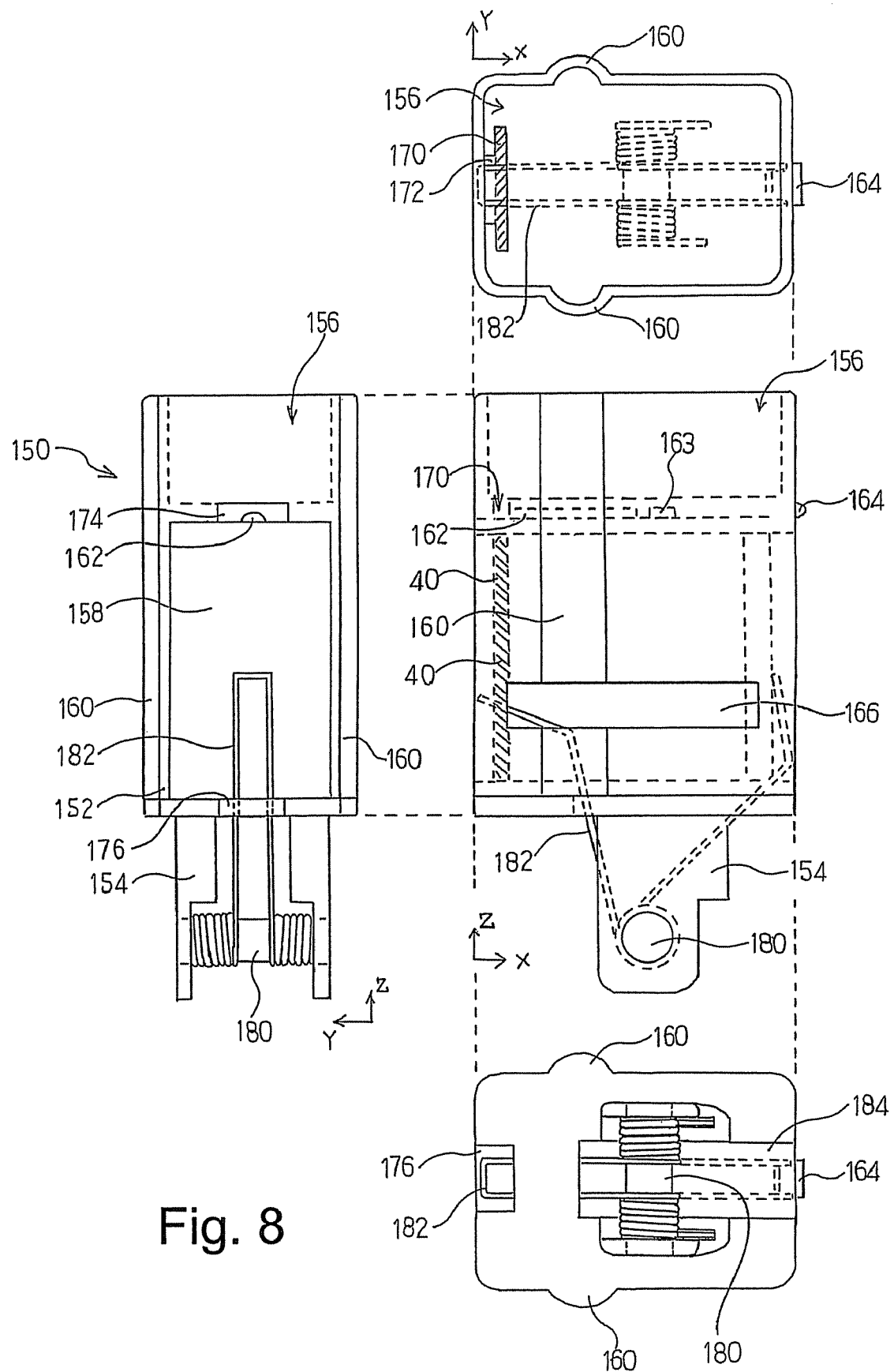
FIG. 8 consists of four drawings illustrating a magazine holder according to an embodiment of the present invention.

The magazine holder 150 illustrated in FIG. 8 can hold the test piece magazine 200. As illustrated in FIG. 3, the magazine holder 150 is positioned between the portable specimen analyzer 10 and the cylindrical casing 110. When a user pushes the portable specimen analyzer 10 downward relative to the cylindrical casing 110, the magazine holder 150 has a function to initiate an extrusion mechanism to work. The magazine holder 150 can store a plurality of specimen component test pieces which are pressed and aligned in a predetermined direction under an external bias force and are exchangeable. According to the arrangement illustrated in FIG. 3, the torsion spring 182 generates an external bias force.

The magazine holder 150 includes a framed casing 152 that has a storage space for guiding and supporting side surfaces of the test piece magazine 200 which is exchangeable. The magazine holder 150 includes a spring installation base 154 to which the torsion spring 182 is attached. The spring installation base 154 is provided on the bottom surface of the framed casing 152. Furthermore, the magazine holder 150 includes the distal-edge guide portion 156 to which the distal end portion of the portable specimen analyzer 10 can be inserted. The distal-edge guide portion 156 is provided on the upper surface of the framed casing 152. As described above, the magazine holder 150 is a compact device capable of holding the test piece magazine 200 installed therein, giving a bias force to the specimen component test pieces 40 stored in the test piece magazine 200, installing an urging member, and receiving the distal end portion of the portable specimen analyzer 10 which is operated by a user.

The framed casing 152 (a frame body) includes a storage space 158 to which the test piece magazine 200 can be attached to from which the test piece magazine 200 can be detached. The storage space 158 can hold the test piece magazine 200. The storage space 158 has an inner shape slightly larger than the outer shape of the test piece magazine 200. The framed casing 152 has a sight window 166 provided on a side surface, when seen from the front side. The sight window 166 corresponds to the inspection window 130 provided on the cylindrical casing 110.

Furthermore, the framed casing 152 may include the groove 162 corresponding to the projecting guide 208 provided on the upper surface of the test piece magazine 200. The groove 162 extends in the X direction on a ceiling of the storage space 158. Furthermore, the framed casing 152 includes slits 174 and 176 corresponding to the slit 222 (and to the slit 224) of the test piece magazine 200. The slits 174 and 176 are provided on the left side wall of the framed casing 152. Furthermore, the framed casing 152 includes a cutout opening (window) 184 provided on the bottom surface. The torsion spring 182 can be placed in cutout opening (window) 184. The cutout opening (window) 184 corresponds to the cutout opening (window) 212 formed on the bottom surface of the test piece magazine 200.

Still further, the framed casing 152 may include the lock recess 163 corresponding to the lock projection 209 provided on the upper surface of the test piece magazine 200. The lock recess 163 is formed on the ceiling of the storage space 158. As described above, if a user further pushes the test piece magazine 200, the lock projection 209 engages with the lock recess 163 and accordingly the position of the test piece magazine 200 relative to the magazine holder 150 can be fixed. Furthermore, if a user pushes the test piece magazine 200 in the opposite direction to perform an extrusion operation, the lock projection 209 is disengaged from the lock recess 163. The torsion spring 182 transmits a resilient force to the test piece magazine 200 via the specimen component test piece 40. Therefore, if the lock projection 209 is disengaged from the lock recess 163, the test piece magazine 200 can be automatically extruded out of the storage space 158 of the framed casing 152. With the above-described function, the test piece magazine 200 can be easily removed from the magazine holder 150.

Furthermore, the ridges 160 may extend on a front outer wall and a rear outer wall of the framed casing 152 and the front-edge guide portion 156. The ridges 160 of the framed casing 152 are swelled portions having an increased wall thickness and protruding outward from front and rear outer surfaces thereof. The ridges 160 of the front-edge guide portion 156 are swelled portion shave the same wall thickness and protrusion outward. The ridge 160 has an outer shape corresponding to that of the groove 114 of the cylindrical casing 110. The ridge 160 and the groove 114 can function as a guide mechanism that enables the magazine holder 150 to move in the Z direction in the cylindrical casing 110. Furthermore, the ridge 160 of the front-edge guide portion 156 has an inner wall (recessed wall) corresponding to the guide ridge 32 formed on the distal end portion of the portable specimen analyzer 10. The inner recessed wall of the ridge 160 and the guide ridge 32 can function as a guide mechanism that enables the distal end portion of the portable specimen analyzer 10 to move in the distal-edge guide portion 156.

As described above, in the framed casing 152, the slits 174 and 176 are formed on the left side wall. The slit 174 formed on the upper surface of the left side wall is connected to the slit 172 formed on the bottom surface of the distal-edge guide portion 156. Furthermore, the slit 172 is continuously formed with a feed outlet 170 on the bottom surface of the distal-edge guide portion 156. The feed outlet 170 is an aperture from which the specimen component test piece 40 is extruded. The feed outlet 170 corresponds to the feed port 220 of the test piece magazine 200. Furthermore, the feed outlet 170 is disposed at a position corresponding to the test piece holding portion 30 of the portable specimen analyzer 10, when the distal end portion of the portable specimen analyzer 10 is inserted into the distal-edge guide portion 156.

As described with reference to FIG. 7, one specimen component test piece 40 is extruded upward out of the test piece magazine 200 by the above-described function of the extrusion projection 122. The test piece holding portion 30 of the portable specimen analyzer 10 receives the extruded specimen component test piece 40 via the feed port 220 of the test piece magazine 200 and the feed outlet 170 of the magazine holder 150. The test patch 42 can be positioned so as to face the sensing portion 24.

The magazine holder 150 has the stopper projection 164 provided on an outer surface of the right side wall in the vicinity of the boundary between the framed casing 152 and the front-edge guide portion 156. The stopper projection 164 is a projection protruding from the outer shape of the magazine holder 150. In at ordinary state, the stopper projection 164 prevents the magazine holder 150 from been pushed into the cylindrical casing 110. As described above, the cylindrical casing 110 has the groove 118 corresponding to the stopper projection 164. The stopper projection 164 is capable of holding the magazine holder 150 in an ordinary position, as described above in relation to the groove 118 of the cylindrical casing 110.

The spring installation base 154 of the magazine holder 150 supports an installation shaft 180 extending in the Y-axis direction around which the torsion spring 182 is attached. The torsion spring 182 is an urging member capable of generating a resilient force for pressing the specimen component test pieces 40 aligned in the test piece magazine 200. More specifically, the torsion spring 182 has one end (anchor portion) fixed to the installation shaft 180. The torsion spring 182 can rotate around the installation shaft 180 and, at its distal end portion, can generate the resilient (urging) force acting in the X-axis direction (i.e., a direction normal to the Y axis). The distal end (i.e., front end) portion of the torsion spring 182 pushes a rear face of the biasing plate 204 placed in the test piece magazine 200, in a state wherein the test piece magazine 200 is installed on the magazine holder 150. The torsion spring 182 resiliently presses the biasing plate 204 in the X-axis direction. As illustrated in FIG. 3, under the resilient (urging) force of the torsion spring 182, the biasing plate 204 pushes the specimen component test pieces 40 aligned in the test piece magazine 200 toward the feed port 220.

As described above, in a state wherein the test piece magazine 200 is installed on the magazine holder 150, the torsion spring 182 generates the resilient force acting in the X direction to press the specimen component test pieces 40 aligned in the test piece magazine 200 toward the feed port 220. Accordingly, if a leasing specimen component test piece 40 is extruded from the feed port 220, the next specimen component test piece 40 moves forward under the resilient force of the torsion spring 182 and stops at the position corresponding to the feed port 220. More specifically, the torsion spring 182 acts as a member capable of urging the plurality of specimen component test pieces 40 aligned in a predetermined order and successively conveying the test pieces 40 toward the outlet (i.e., toward the feed port 220).

Figure 9:
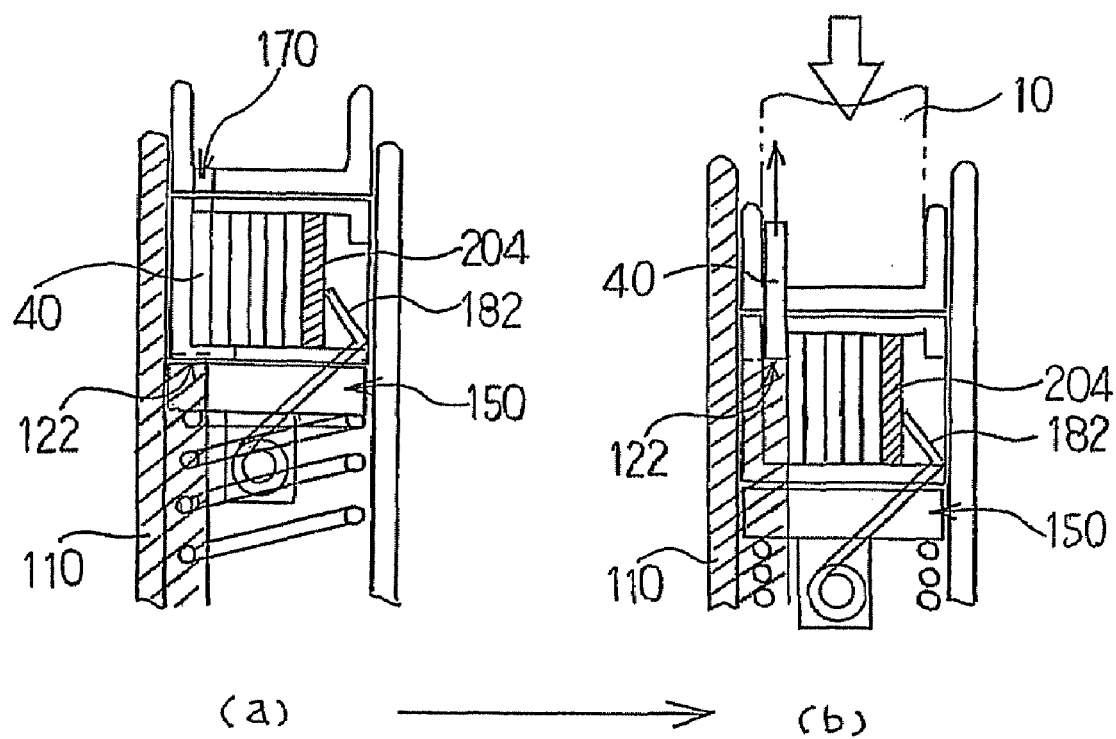
FIG. 9 illustrates an extrusion function of the test piece feeder according to an embodiment of the present invention.

FIG. 9 illustrates an extrusion function of the test piece feeder 100 having the above-described arrangement, in which the left-side view (a) illustrates the magazine holder 150 positioned at an ordinary position relative to the cylindrical casing 110. In this state, the extrusion projection 122 of the cylindrical casing 110 does not contact with the foremost specimen component test piece 40 in the magazine holder 150. The torsion spring 182 and the biasing plate 204 press each specimen component test piece 40 toward the feed outlet 170 in the test piece magazine 200 installed on the magazine holder 150.

The right-side view (b) illustrates the portable specimen analyzer 10 inserted into the distal-edge guide portion of the magazine holder 150 which is pushed downward as illustrated by an large arrow mark. In this state, the extrusion projection 122 of the cylindrical casing 110 contacts with the foremost specimen component test piece 40 in the magazine holder 150 and extrudes the test piece 40 upward. More specifically, if a user pushes the portable specimen analyzer 10 in the large arrow mark direction, the magazine holder 150 moves downward relative to the extrusion projection 122. As a result, the extrusion projection 122 pushes the specimen component test piece 40 upward.

Figure 10:
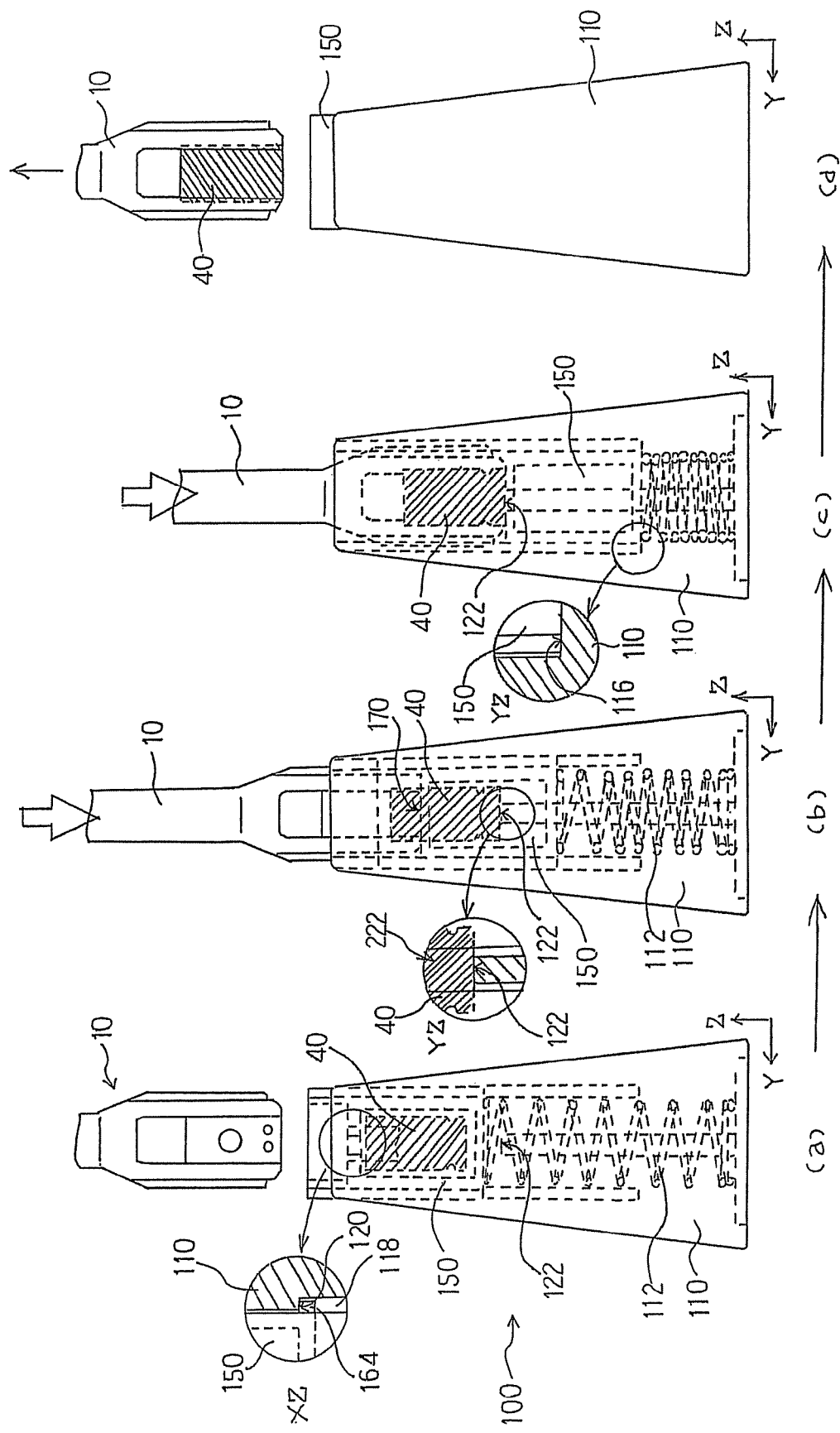
FIG. 10 consists of four time-sequential drawings illustrating an exemplary operation for sending and attaching a new specimen component test piece to a portable specimen analyzer according to an embodiment of the present invention.

FIG. 10 illustrates sequential operations for automatically feeding and attaching a new specimen component test piece 40 to the portable specimen analyzer 10 with a user's operation for pushing the portable specimen analyzer 10 into the test piece feeder 100, from left to right, in order of (a), (b), (c), and (d). The drawing (a), illustrated along the YZ-plane, illustrates a state wherein the portable specimen analyzer 10 is not yet inserted in the test piece feeder 100. In this state, the magazine holder 150 is in an ordinary position relative to the cylindrical casing 110. The upper-limit edge 120 of the groove 180 of the cylindrical casing 110 restricts the stopper projection 164 of the magazine holder 150. The coil spring 112 generating a resilient force and the upper-limit edge 120 (i.e., a restriction member) can hold the magazine holder 150 at the ordinary position. In the ordinary position, the extrusion projection 122 of the cylindrical casing 110 does not contact with the specimen component test piece 40.

The drawing (b), i.e., the view following the drawing (a), illustrates the portable specimen analyzer 10 inserted in the distal-edge guide portion of the test piece feeder 100, where the portable specimen analyzer 10 is pushed down against the resilient force of the coil spring 112 as indicated by a large arrow mark. In the state illustrated in the drawing (b), the extrusion projection 122 of the cylindrical casing 110 relatively moves in the slit 222 and pushes the engaged specimen component test piece 40 upward.

The drawing (c), i.e., the view following the drawing (b), illustrates a state wherein the portable specimen analyzer 10 is further pushed down as indicated by a large arrow mark and stopped at the lowermost end. In the state illustrated in the drawing (c), the magazine holder 150 contacts with the lower-limit end 116 of the groove formed on the cylindrical casing 110 and cannot move downward. In this state, the specimen component test piece 40 extruded from the magazine holder 150 is completely extruded out of the test piece magazine by the extrusion projection 122, and is conveyed into the test piece holding portion of the distal end portion of the portable specimen analyzer 10. Accordingly, the position of the magazine holder 150 in this state is referred to as "extrusion position."

The drawing (d), i.e., the view following the drawing (c), illustrates a state wherein the portable specimen analyzer 10 is raised upward. In this state, a new specimen component test piece 40 is attached on the portable specimen analyzer 10. In this case, the magazine holder 150 returns to the ordinary position (i.e., the state illustrated in the drawing (a)) again under the resilient force of the coil spring of the cylindrical casing 110. Thus, if a user wants to attach a new specimen component test piece 40 on the portable specimen analyzer 10, the user can insert the portable specimen analyzer 10 into the test piece feeder 100 and push the portable specimen analyzer 10 until it reaches the lowermost position. As described above, a user can attach a new specimen component test piece 40 to the portable specimen analyzer 10 with a simple (one-touch) operation for inserting the portable specimen analyzer 10 into the test piece feeder 100 and pushing the portable specimen analyzer 10 downward.

What is claimed is:

1. A test piece magazine capable of storing a plurality of specimen component test pieces aligned in a predetermined direction under an external bias force and extruding a specimen component test piece via a feed outlet under an external extrusion force, comprising:

a boxlike casing having an inner space storing a plurality of specimen component test pieces aligned in a thickness direction;

an aperture formed in at least a rear side surface portion of the boxlike casing to which a rear side surface of a biasing plate faces, and supplying a bias force to the biasing plate;

a test piece outlet formed at an upper surface portion of the boxlike casing via which a foremost specimen component test piece can be extruded in an up-and-down direction; and a slit provided in a front side surface portion of the boxlike casing to which the specimen component test pieces are pressed, the slit extending over a full length of the front side surface portion from a lower surface portion of the boxlike casing to the upper surface of the boxlike casing with a uniform width for supplying an extrusion force to extrude the specimen component test piece upward, wherein, at the lower surface portion of the boxlike casing, the slit has an extrusion length in the thickness direction of the specimen component test piece, the extrusion length being equivalent to the sum of the thickness of the front side surface portion of the boxlike casing and the thickness of the specimen component test piece, on the upper surface portion of the boxlike casing, the slit is connected to the test piece outlet and has a length corresponding to the extrusion length in the thickness direction of the specimen component test piece, and the external extrusion force can be applied to the specimen component test piece using an extrusion surface defined by the extrusion length and the slit width.

2. The test piece magazine according to claim 1, wherein the length of the inner space of the boxlike casing in an alignment direction of the specimen component test pieces is equivalent to the following equation:

(maximum number of the specimen component test pieces storable in the inner space)×(thickness of one of the specimen component test pieces)+ (thickness of the biasing plate).

3. The test piece magazine according to claim 1, wherein the biasing plate is disposed in the inner space of the boxlike casing, with one side face of the biasing plate contacting a rearmost specimen component test piece and the other side surface of the biasing plate receiving the bias force applied to the specimen component test pieces in the alignment direction.

4. The test piece magazine according to claim 3, wherein the biasing plate has an outer shape and dimensions similar to those of the specimen component test piece, such that the biasing plate can be extruded via the feed outlet when the external extrusion force is applied to the biasing plate.

5. The test piece magazine according to claim 3, wherein a marking is provided on a rearmost specimen component test piece which is finally extruded to enable a user to discriminate the rearmost specimen component test piece from other specimen component test pieces when the boxlike casing stores the plurality of specimen component test pieces aligned in the thickness direction.

6. The test piece magazine according to claim 1, wherein a marking is provided on a rearmost specimen component test piece which is finally extruded to enable a user to discriminate the rearmost specimen component test piece from other specimen component test pieces when the boxlike casing stores the plurality of specimen component test pieces aligned in the thickness direction.

* * * * *